(12) United States Patent
Knight

(10) Patent No.: US 9,766,163 B2
(45) Date of Patent: Sep. 19, 2017

(54) GAS PROBES

(71) Applicant: Endet Ltd., Market Drayton, Shrosphire (GB)

(72) Inventor: Jeremy Knight, Market Drayton (GB)

(73) Assignee: Endet Ltd., Shropshire (GB)

( * ) Notice: Subject to any disclaimer, the term of this patent is extended or adjusted under 35 U.S.C. 154(b) by 0 days.

(21) Appl. No.: 15/386,616

(22) Filed: Dec. 21, 2016

(65) Prior Publication Data

US 2017/0102298 A1 Apr. 13, 2017

Related U.S. Application Data

(63) Continuation of application No. 13/858,056, filed on Apr. 7, 2013, now Pat. No. 9,528,917, which is a (Continued)

(30) Foreign Application Priority Data

Dec. 10, 2005 (GB) .................................. 0525185.5
Nov. 23, 2006 (GB) .................................. 0623351.4

(51) Int. Cl.
*G01N 1/22* (2006.01)
*G01K 1/08* (2006.01)
*G01K 13/02* (2006.01)

(52) U.S. Cl.
CPC ............. *G01N 1/2247* (2013.01); *G01K 1/08* (2013.01); *G01K 13/02* (2013.01); *G01N 1/2294* (2013.01); *G01K 2013/024* (2013.01)

(58) Field of Classification Search
None
See application file for complete search history.

(56) References Cited

U.S. PATENT DOCUMENTS

| 1,994,884 A | 3/1935 | Chew |
| 2,087,723 A | 7/1937 | McCord |

(Continued)

FOREIGN PATENT DOCUMENTS

| AU | 45032/85 | 7/1985 |
| EP | 0586992 | 3/1994 |

(Continued)

OTHER PUBLICATIONS

Search Report in Counterpart GB Patent Application No. 0525185, Jul. 28, 2006, Endet Ltd.

(Continued)

*Primary Examiner* — Robert R Raevis
(74) *Attorney, Agent, or Firm* — Fleit Gibbons Gutman Bongini & Bianco PL; Paul D. Bianco; Gary S. Winer

(57) ABSTRACT

An insertion-type probe main body for insertion into a pipe transporting gas and a method for making such an insertion-type probe main body are provided. The probe main body includes: an elongate upper tubular portion; an elongate lower tubular portion which is integral with and having a diameter smaller than the upper tubular portion; a bore which extends between the upper and lower tubular portions; and helical fins integrally formed on the lower tubular portion and which wind along and around an outer surface of the lower tubular portion and which overlap each other. A radial extension of the lower tubular portion plus helical fins corresponds to an external radius of the upper tubular portion, so that the helical fins extend in a streamline fashion from the upper tubular portion. Numerous other aspects are provided.

13 Claims, 8 Drawing Sheets

Related U.S. Application Data continuation of application No. 12/096,836, filed as application No. PCT/GB2006/004595 on Dec. 8, 2006, now Pat. No. 8,424,396.

(56) References Cited

U.S. PATENT DOCUMENTS

| | | | |
|---|---|---|---|
| 2,293,473 | A | 8/1942 | Schlueter |
| 2,926,527 | A | 3/1960 | Crandall |
| 2,976,128 | A | 3/1961 | Latham, Jr. et al. |
| 3,076,533 | A | 2/1963 | Scruton |
| 3,382,717 | A | 5/1968 | Keppel et al. |
| 4,018,089 | A | 4/1977 | Dzula |
| 4,020,697 | A | 5/1977 | Jander |
| 4,150,574 | A | 4/1979 | Wolf |
| 4,274,417 | A | 6/1981 | Delpy |
| 4,444,022 | A | 4/1984 | Holt et al. |
| 4,485,684 | A | 12/1984 | Weber et al. |
| 4,494,403 | A | 1/1985 | Bowers |
| 4,502,392 | A | 3/1985 | Rosenberger |
| 4,749,415 | A | 6/1988 | Barton |
| 4,762,009 | A | 8/1988 | Scrudto |
| 4,796,696 | A * | 1/1989 | Stocton .............. A61M 5/44 165/169 |
| 4,911,026 | A | 3/1990 | Keives |
| 4,948,264 | A | 8/1990 | Hook, Jr. |
| 4,991,976 | A | 2/1991 | Byles |
| 4,995,256 | A | 2/1991 | Norlien et al. |
| 4,998,954 | A | 3/1991 | Burr |
| 5,052,425 | A | 10/1991 | Hohenberg |
| 5,092,849 | A | 3/1992 | Sampson |
| 5,317,932 | A | 6/1994 | Westlake, III et al. |
| 5,435,999 | A | 7/1995 | Austin |
| 5,537,879 | A | 7/1996 | Malczewski |
| 5,811,696 | A | 9/1998 | Jobson |
| 5,879,948 | A | 3/1999 | Van Pelt et al. |
| 5,895,868 | A | 4/1999 | Giammaruti et al. |
| 5,907,107 | A | 5/1999 | Welker |
| 6,293,163 | B1 | 9/2001 | Johnston et al. |
| 6,390,670 | B1 | 5/2002 | Nimberger |
| 6,539,312 | B1 | 3/2003 | Nimberger |
| 6,557,428 | B2 | 5/2003 | Wickland et al. |
| 7,337,654 | B2 | 3/2008 | Tomita et al. |
| 7,465,086 | B1 | 12/2008 | Foreman, Jr. |
| 8,424,396 | B2 | 4/2013 | Knight |
| 9,188,489 | B2 | 11/2015 | Kleven |
| 9,250,108 | B2 | 2/2016 | Wiklund |
| 9,528,917 | B2 | 12/2016 | Knight |
| 2004/0000991 | A1 | 1/2004 | Schiffmann et al. |
| 2004/0074319 | A1 | 4/2004 | Silvis et al. |
| 2004/0099143 | A1 | 5/2004 | Welker |
| 2004/0152806 | A1* | 8/2004 | Koga .............. C08K 5/103 524/115 |
| 2005/0038172 | A1 | 2/2005 | Nimberger |
| 2005/0223829 | A1 | 10/2005 | Mayeaux |
| 2007/0195857 | A1 | 8/2007 | Krishnamurthy et al. |
| 2008/0031306 | A1 | 2/2008 | Yamada et al. |
| 2008/0190218 | A1 | 8/2008 | Riazanskaia |

FOREIGN PATENT DOCUMENTS

| | | |
|---|---|---|
| GB | 2335994 A | 10/1999 |
| GB | 2359070 | 8/2001 |
| JP | 55159135 A2 | 12/1980 |
| JP | 08226869 | 9/1996 |
| JP | 11023373 | 1/1999 |
| JP | 3126141 U | 10/2006 |
| RU | 2224990 | 2/2004 |

OTHER PUBLICATIONS

Search Report in Counterpart GB Patent Application No. 0525185, Dec. 6, 2006, Endet Ltd.
International Search Report from counterpart PCT/GB2006/004595, Nov. 15, 2007, Knight.
Examination Report in Counterpart GB Patent Application No. 0525185, Jan. 30, 2008, Endet Ltd.
Written Opinion from counterpart PCT/GB2006/004595, Jun. 10, 2008, Knight.
Int'l Prelim Report on Patentability from counterpart PCT/GB2006/004595, Jun. 11, 2008, Knight.
Reply to Examination Report in Counterpart GB Patent Application No. 0525185, Apr. 30, 2008, Endet Ltd.
Examination Report in Counterpart GB Patent Application No. 0525185, May 20, 2008, Endet Ltd.
Reply to Examination Report in Counterpart GB Patent Application No. 0525185, May 27, 2008, Endet Ltd.
Examination Report in Counterpart CN Patent Application No. 200680052243, Jun. 19, 2009, Endet Ltd.
Examination Report in Counterpart CN Patent Application No. 200680052243, Mar. 26, 2010, Endet Ltd.
Examination Report in Counterpart EA Patent Application No. 200870032, Apr. 27, 2010, Endet Ltd.
Examination Report in Counterpart CN Patent Application No. 200680052243, Aug. 24, 2010, Endet Ltd.
M. Zdravkovich, "Review and Classification of Various Aerodynamic and Hydrodynamic Means fro Suppressing Vortex Shredding," Journal of Wind Engineering and Industrial Aerodynamics, 7:145-189 (1981).
"Guide for Evaluation of Flow-Induced Vibration of a Cylindrical Structure in a Pipe," Japan Soc. Mech. Eng, S-012-1988 (Sep. 1988) (English Translation).
Japan Soc. Mech. Eng. Handbook p. A3-126 (undated) (English Translation).
Shigehiko Kaneko et al., eds., "Flow-Induced Vibrations: Classification and Lessons from Practical Experiene" (undated).
Supplemental Examination filed Mar. 26, 2017, U.S. Appl. No. 96/000,207.
Reexam Litigation Search Conducted mailed Mar. 31, 2017 for U.S. Appl. No. 96/000,207.
Reasons for SNQ Determination mailed Apr. 25, 2017 for U.S. Appl. No. 96/000,207.
Issuance of Supplemental Examination Certificate mailed Apr. 25, 2017 for U.S. Appl. No. 96/000,207.
C. Scruton and D.E.J. Walshe, "A Means for Avoiding Wind-Excited Oscillations of Structures with Circular or Nearly Circular Cross-Section," NPL Aero Report 335, Oct. 1957.
Declaration Under 37 CFR § 1.131 of Inventor Jeremy Knight submitted Mar. 26, 2017 for U.S. Appl. No. 96/000,207.
Office Action dated Jun. 22, 2017 for Ex Parte Reexamination No. 96/000,207.

* cited by examiner

GAS PROBES

BACKGROUND

This invention relates to an improved thermowell or fluid sampling probe for use in chemical processing vessels, pipelines and the like.

Gas sampling probes, for example the insertion type, wherein a sample of gas has to be dynamically taken from a pipeline or large vessel, are well known but suffer from a number of problems due to the flowing nature of the fluids to be sampled and the required length of the probe.

There are a number of problems associated with thermowell probes and gas sampling probes for use with natural gas pipelines. For example, in designing such probes to meet the mechanical requirements of the installation may result; in a probe that has a large volume and generates significant turbulence. This again is incompatible with sampling requirements. Thus, such probes typically suffer from the following drawbacks: they have a large internal volume, which is incompatible with 'real time' analysis and environmental considerations, they are prone to inaccurate sampling (due to turbulence), and mechanical failure of the probe can result due to resonance failure that are a consequence of vortex shedding. These three drawbacks are described more fully below.

Firstly, following recognized guidelines for sampling natural gas, such as ISO 10715:2001, which states that samples should be taken from the middle ⅓ of the pipe, results in a "long" sample probe. Not only does the probe have to be at least ⅓ the diameter of the pipe (pipe size is often 2 ft-4 ft in diameter/600 mm to 1200 mm) but also the length has to be sufficient to connect the probe via a branch tee and flange or if permitted, by a threadolet. (Normally branch flanges are the preferred connection type). In many cases the length of a gas sampling probe is significantly, or even hugely increased by the requirement, for a retractable and isolatable probe. In this case the probe is connected by a branch tee, valve and flange combination.

Secondly, there is the need to consider the phenomena of vortex shedding and the possibility that the vortex shedding frequency may coincide with the natural frequency of the probe. Should the two coincide then it is very likely that the probe will fail (snap off) due to resonance effects.

The combination of the two points above forces a probe design of a fattish nature. (Normally a probe with about a 25 mm (1") outside diameter). Due to the way tubes and pipes are manufactured, it is not economical/normal, to manufacture a tube of say 1" OD (25 mm) with an ID of less than ½" (12.5 mm).

In the case of gas sampling probes the combination of the 'long' length of the probe combined with the 'relatively' large internal diameter results in a significant gas hold up volume in the sample probe itself. This stored gas is often known as 'dead space' gas and has to be vented, or otherwise disposed of, before actual gas from the pipeline can enter the analyzer. The volume of stored or 'dead space' gas within the probe is further increased by the effect of pressure. For each bar of the pressure that the pipeline operates above atmospheric pressure, then the real (or normal or standard) volume of gas in the probe is increased by that ratio. For example if the internal volume of the probe was say 0.25 liters and the pressure of the pipeline it is operating in is 40 bara then the real (or normal or standard) volume of stored or 'dead gas' within the probe will be approximately 0.25× 40=10 liters. It is not uncommon for gas pipelines to be operating at 80 bara or even higher.

Thus, there is a problem designing a gas sampling probe with a response time fast enough to match an associated analytical system. In such circumstances a significant amount, of gas that has to be moved out of the way (vented) before a representative sample of the actual gas in the pipeline can be presented/introduced to the analyzer/sample cylinder connected to the sample probe. This venting process can be very damaging to the environment.

An alternative to using a pipe or tube would be to use a solid bar with a small hole 'drilled' down the middle. However, drilling a 2, 3, 4, 5 mm diameter hole or even larger, down the length of a stainless steel bar of typically say 0.3 to 2.0 meters long is no easy or cheap task. Additionally, the quality of the surface finish of such a drilled hole is difficult to control which brings its own problems to representative sampling of natural gas, especially with the higher hydrocarbons and reactive components.

Lastly, by introducing such a large protrusion into the flowing gas creates significant, turbulence which in turn can momentarily alter the composition of the gas. Small droplets of hydrocarbon liquid may be formed, similar to the white vapor trails often seen behind an airplane (except in the case of the airplane it is waiter droplets not: hydrocarbon liquid droplets). These small droplets not only change the gaseous phase composition but also have the potential to absorb, momentarily, any reactive components such as hydrogen sulphide. Therefore at the point in space (actually the point in the pipeline at the tip or entrance to the sample probe) where the gas is sampled from, every effort needs to be made to reduce the turbulence.

An object of this invention is to reduce the internal volume of a gas sampling probe. Another object of the invention is to minimize or eliminate vortex shedding induced by use of such a probe. A further object of the invention is to minimize the turbulence at the sampling point.

SUMMARY

In an aspect: of the invention, a gas sampling probe is provided that includes an elongate member having an inlet end and an outlet end, and a sampling passage, disposed within the member. The sampling passage extends from the inlet end to the outlet end. The inlet end comprises a curved outer surface.

Another aspect of the invention provides a gas sampling probe including an elongate main tubular member having an inlet end and an outlet end and a sampling tube housed within the main tubular member. The sampling cube extends from the inlet end to the outlet end. The cross sectional area of the sampling tube is 0.1 to 30 mm$^2$.

Another aspect of the invention provides a gas sampling probe having an elongate main tubular member having an inlet end and an outlet end and a sampling tube housed within the main tubular member. The sampling tube extends from the inlet end to the outlet end. The main body has at least one helical fin attached to and wound around the outer surface of the main, tubular member, or integrally formed, as part of the main tubular member. The thickness of the fin, while not being critical, is preferably in the range 0.005 D to 0.2 D; where D is a diameter of the main tubular member. The depth of the fin is preferably in the range 0.05 D to 0.25 D; where D is the diameter of the main tubular member.

Preferably, the gas sampling probe includes a sampling tube housed within the main tubular member. The sampling tube extends from the inlet end to the outlet end. The cross sectional, area of the sampling tube is 0.1 to 30 mm².

In some aspects, preferably the inner surface of the sampling tube has a surface roughness below 0.8µ roughness average (RA). Preferably, the inner surface of the sampling tube is treated by electro-polishing in order to reduce surface roughness. The inner surface of the sampling tube may be further treated with a passivation process to reduce surface activity such as a silicone based chemical vapor deposition process of which Silcosteel® or Sulfinert® coatings are specific examples. The gas sampling probe may be fabricated using stainless steel.

Preferably, the gas sampling probe further includes an end member with a smooth curved outer surface, located at the inlet end, and configured to provide a seal between an outer surface of the sampling tube and an inner surface of the main tubular member. The curved outer surface may predominantly correspond to a surface formed by revolving a smooth curve about the centre axis of the sample tube and/or tubular member. The curved outer surface may be formed by a partial ellipsoid, partial catenoid, partial conoid or partial paraboloid of revolution. Preferably, the smooth outer surface has a surface roughness less than 0.4µ RA. The smooth outer surface may be further treated with a passivation process to reduce surface activity and particulate build up such as a silicon based chemical vapor deposition process of which Silcosteel®-AC is a specific example.

Another aspect of the invention provides a gas sampling probe including an elongate main tubular member having an inlet end and an outlet end. The main body has at least, one helical fin. This fin may be attached to and wound around the outer surface of the main tubular member, or may be formed integrally with the main tubular member.

The addition of the helical fins, of course, eliminates the requirement for increasing the thickness and mass due to natural frequency considerations however the fins themselves are structural and may be taken into, consideration to reduce the stresses due to the straightforward loads due to velocity etc which would/can by itself reduce the mass of the gas sampling probe. Preferably the probe further comprises a sampling tube housed within the main tubular member. The sampling tube extends from the inlet end to the outlet end.

Preferably, the sampling probe has a hemispherical inlet end. The fluid inlet of the sampling probe may be located on the surface of the inlet end of the probe, where surface conditions are controlled. A sampling tube may pass throughout the whole length of the probe. Preferably, helical, fins are provided on the exterior portion of the probe, that in use, lies within the flowing stream of the gas.

Preferably, the internal bore of the sampling tube has a special surface treatment such as electro polishing and/or for critical analysis conditions either the Silcosteel® or Sulfinert® surface coating.

Preferably, the hemispherical end with controlled surface conditions is treated with the Silcosteel®-AC surface coating.

Another aspect of the invention provides a gas sampling probe including an elongate main tubular member having an inlet end and an outlet end. The main, body has at least one helical fin. This fin may be attached to and wound around the outer surface of the main tubular member, or may be formed integrally with the main tubular member. Preferably the probe further comprises a sampling tube housed within the main tubular member. The sampling tube extending from the inlet end to the outlet end.

Preferably, the gas sampling probe includes a sampling tube housed within the main tubular member. The sampling tube extends from the inlet end to the outlet end. The cross sectional area of the sampling tube is 0.1 to 30 mm².

Preferably, the sampling probe; has a hemispherical inlet end. The fluid inlet of the sampling probe may be located on the surface of the inlet end of the probe, where surface conditions are controlled. A sampling tube may pass throughout the whole length of the probe. Preferably, helical fins are provided on the exterior portion of the probe, that in use, lies within the flowing stream of the gas.

Preferably, in use the longitudinal axis of the gas sampling probe is be inclined at an angle α to the axis of a pipe or conduit carrying fluid that is to be sampled, where α is in the range 90° to 45°. The gas sampling probe of the invention is preferably used as part of a retractable sampling probe system. Thus in use, allowing retraction of the sampling probe, at least in part, out of the flow of fluid to be sampled. Preferably, only the last ⅓ of the portion of the probe that lies within the flowing fluid has helical fins. However, often helical fins will extend along most or all of the portion of the probe that lies within the fluid flow from which samples are to be taken.

Another aspect of the invention includes a method of using a gas sampling probe according to the above mentioned aspects. In use the longitudinal axis of the gas sampling probe may be inclined at an angle α to the axis of a pipe or conduit carrying fluid that is to be sampled, where α is in the range 90° to 45°. The gas sampling probe of the invention is preferably used as part of a retractable sampling probe system. Thus in use, allowing retraction of the sampling probe, at least in part, out of the flow of fluid to be sampled. Preferably, only the last ⅓ of the portion of the probe that lies within the flowing fluid has helical fins. However, often helical fins will extend along most or all of the portion of the probe that lies within the fluid flow from which samples are to be taken.

In their simplest form thermowells comprise a tube, sealed at one end and with a fitting at the other end to facilitate attachment to the wall of a pressure vessel, pipeline etc. Such a device typically allows a temperature sensor, such as a thermocouple, to be inserted within the thermowell tube. The thermowell thus allows the sensor to be in reasonably close thermal contact to a fluid the temperature of which is to be measured. It also protects the sensor from direct contact with this fluid and so avoids mechanical damage to the probe.

When thermowells or gas sampling probes are used in certain applications, such as high pressure or high velocity pipelines, a known problem is deformation or fracture of the probe in response to cyclic stresses induced in the probe as a result of fluid flow. This is a particular problem at high velocities and can result from vortex shedding from points around the probe.

An object of the present invention is to provide a thermowell that is less susceptible to this type of damage. A farther object of this invention is to minimize or eliminate vortex shedding induced by use of the probe.

For a thermowell to provide a good and fast response, to allow temperature changes of the fluid being measured by the temperature sensor contained within the thermowell "quickly and accurately," the thermowell should preferably be of the thinness section possible and preferably of the minimum mass possible. The requirements of designing a thermowell to resist both the straightforward loads due to velocity etc and to design it so that the natural frequency is "away" from any vortex shedding frequency is incompatible with this requirement.

Another aspect of the invention includes a thermowell having an elongated tube with one or more helical fins wound longitudinally around at least part of the outer surface of the tube. The addition of the helical fins, of course, eliminates the requirement for increasing the thickness and mass due to natural frequency considerations however the fins themselves are structural and may be taken into consideration to reduce the stresses due to the straightforward loads due to velocity etc. which would/can by itself reduce the wall thickness and therefore the mass of the thermowell.

Preferably, the tube is substantially circular in cross section. More preferably, the tube is cylindrical in shape. The tube may be closed at one end, in which case the closure is preferably curved or flat in shape, and is more preferably hemispherical is shape. Preferably, there are 2, 3, 4, 5 or 6 helical fins.

The thermowell tube may have an external diameter in the range 3 to 75 mm. The length of the tube is preferably in the range 10 to 1800 mm. In use, the length of tube inserted within flowing fluid is preferably in the range 3.0 to 1500 mm. The tube preferably has an internal bore the internal diameter of which is in the range 1 to 25 mm.

The thermowell of the invention is preferably used as part of a retractable thermowell system. Thus in use, allowing retraction of the thermowell, at least in part, out of the flow of fluid. This is difficult for conventional thermowells owing to the thickness and mass considerations noted above. A retractable thermowell would have to be thicker and of a greater mass than a fixed thermowell to resist, both types of loads noted above. The reduction in thermowell mass resulting from adding the helical fins allows a retractable design. A retractable thermowell also provides useful benefit for: a) easier service and maintenance, b) easier calibration, c) change out without interruption to the process.

The measurement of flow (or more correctly mass per unit time) of a fluid requires that the primary flow measurement signal is corrected for both the actual temperature and pressure of the fluid being measured. In the case of temperature measurement this normally means that a thermowell is placed in the fluid stream adjacent to the primary flow measurement signal (Generally the rules, "Standards and codes of Practice," require that the temperature is measured from the middle third of a pipeline etc.) Nearly all primary flow measuring devices require a steady/uniform flow pattern upstream and downstream of the device in order to produce an accurate primary flow signal. Adding a thermowell (that protrudes at least to the middle third of the pipeline) adjacent to the primary flow measuring device is incompatible with this requirement as it produces a disturbance in the flow pattern and therefore reduces the accuracy of the primary flow measurement signal. Because the addition, of helical fins to a thermowell provides a much more stable flow pattern around the thermowell than one without, and because the thermowell may well be of a smaller diameter (does not have to be designed to cater for vibration due to vortex shedding) the flow disturbance is much reduced and therefore using a thermowell with helical fins will allow for a more accurate signal from the primary flow measuring device.

In its basic form a thermowell provides two functions: (1) It provides a protection, support and attachment means where a primary temperature measuring device cannot be placed directly at a desired position into the medium whose temperature is to be measured, and (2) It provides a means of transferring the temperature of the medium to the primary temperature measuring device; ideally with the minimum thermal lag (delay in reaching temperature equilibrium with medium)

These requirements are generally in conflict with one another. In many cases this means that a relatively massive thermowell (sleeving, etc.) is required to support/protect the temperature measuring device. This results in a significant thermal lag, which is particularly disadvantageous when measuring fluctuating temperatures; such a system will tend to measure the (time) average temperature and not respond to short-term transients.

Thus, a further object of the present, invention is to provide a thermowell that in use allows a temperature measuring device housed within to react to rapid changes in the fluid temperature being measured and thereby reduces the disadvantages of thermal lag.

In one aspect the invention comprises a thermowell having a first portion having an elongated tube having an inlet end and an outlet end and means of holding at the outlet end a second portion that in use houses a primary temperature measuring device. Preferably, the second portion comprise an open lattice or frame that extends axially away from the outlet end. The lattice/frame may comprise a plurality of similar helically wound fins; wound around a common axis. In another embodiment, the second portion may comprise a tip, made at least in part, of higher thermal conductivity material and/or comprising a thinner: wall member than the first portion; and attached to the outlet end of the first portion. Preferably a thermally insulating element is provided, between the first and second portion or between the second portion and the primary temperature measuring device.

BRIEF DESCRIPTION OF THE DRAWINGS

Features of the present invention can be more clearly understood from the following detailed description considered in conjunction with the following drawings, in which the same reference numerals denote the same elements throughout, and in which.

DETAILED DESCRIPTION

Figure 1:
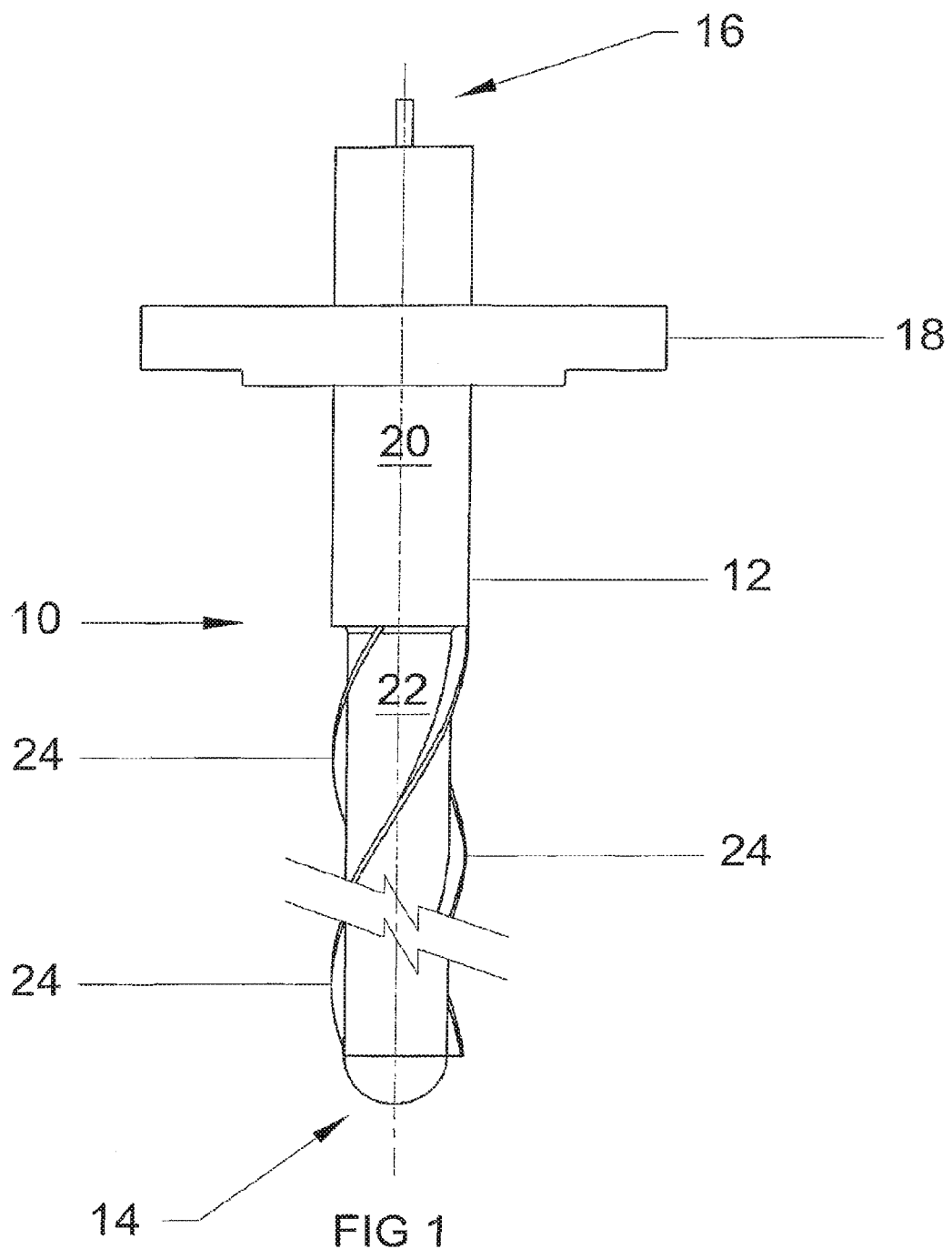
FIG. 1 shows a side view of a gas sampling probe according to a first embodiment of the invention.

FIG. 1 shows a side view of a gas sampling probe according to a first embodiment of the invention. The gas sampling probe 10 comprises an elongate main tubular body 12 with an inlet end 14 and an outlet end 16. A flange 18 is attached to the main body 12 near the outlet end 16. This is in conventional flange that in use allows the probe to be attached in a fluid tight manner to the system being sampled. Main body 12 comprises an upper tubular portion 20 that is integral with a slightly smaller diameter lower portion 22. The difference in diameter between the upper portion 20 and lower portion 22 may be such as to allow several helical fins 24 to be attached in a streamline fashion; that is such that the radial extension of the lower portion 22 plus fin 24 fairly closely corresponds to the external radius of the upper tube portion 20. It should be noted that while a plurality of fins is preferred it is not essential to have three fins; for example two or four fins may be used.

Figure 2:
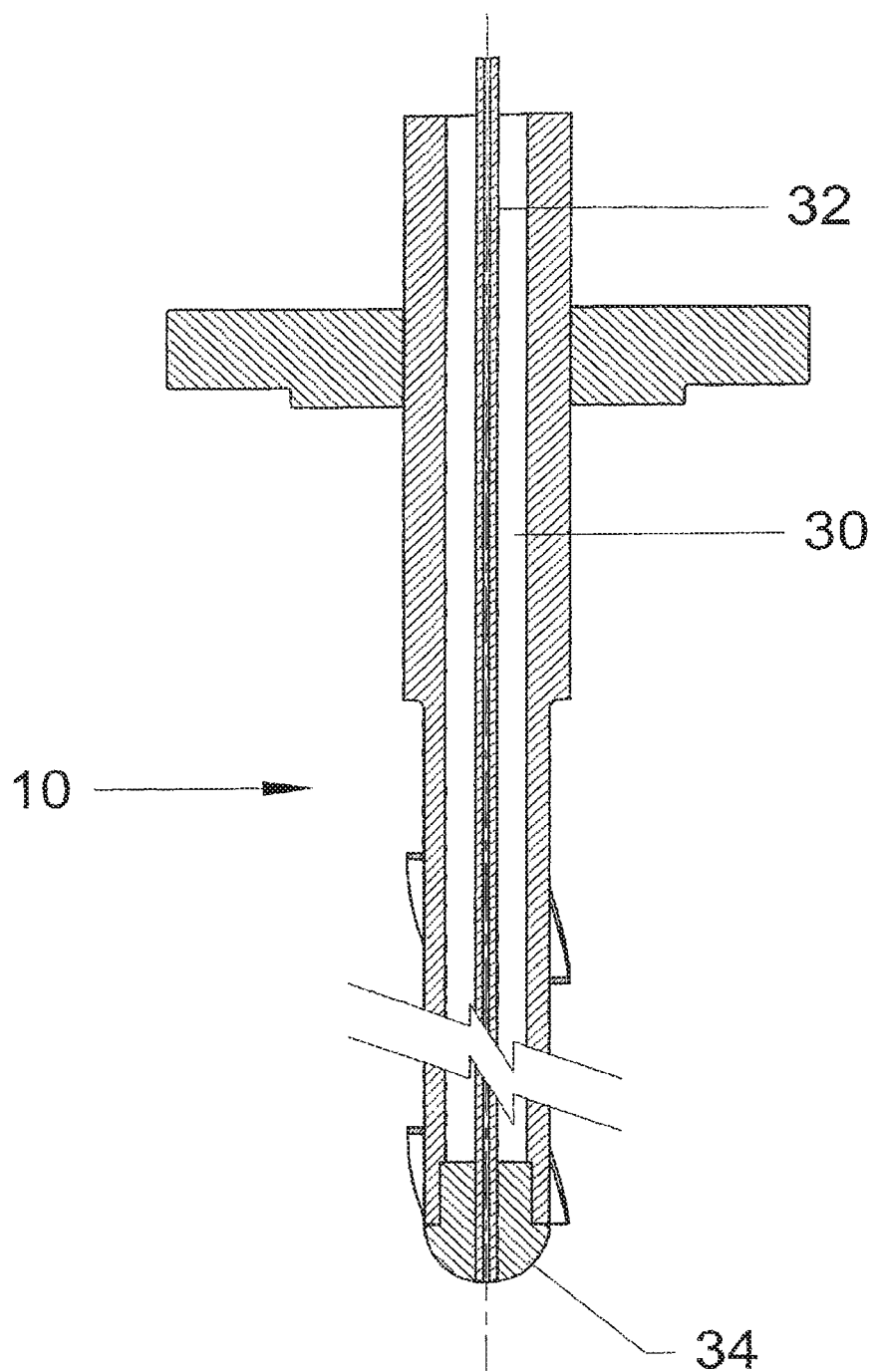
FIG. 2 shows a diametric sectioned view corresponding to FIG. 1.

FIG. 2 shows a diametric sectioned view corresponding to FIG. 1. It can be seen that main body 10 has a constant diameter bore 30. The main body member 10 has a wall thickness selected to provide the structural strength required of the probe in use. A sampling tube 32 is positioned within bore 30, preferably along the central axis of bore 30. Sampling tube 32 is held in place by an end member 34. The sampling tube is preferably constructed from stainless steel, and preferably has an internal diameter of 0.05 to 5 mm; and more preferably a diameter in the range 2 to 4 mm. The sampling tube 32 has a wall thickness selected to provide the structural strength required of the probe in use. Preferably the sampling tube has a wall thickness in the range 0.2 to 2 mm.

Figure 3:
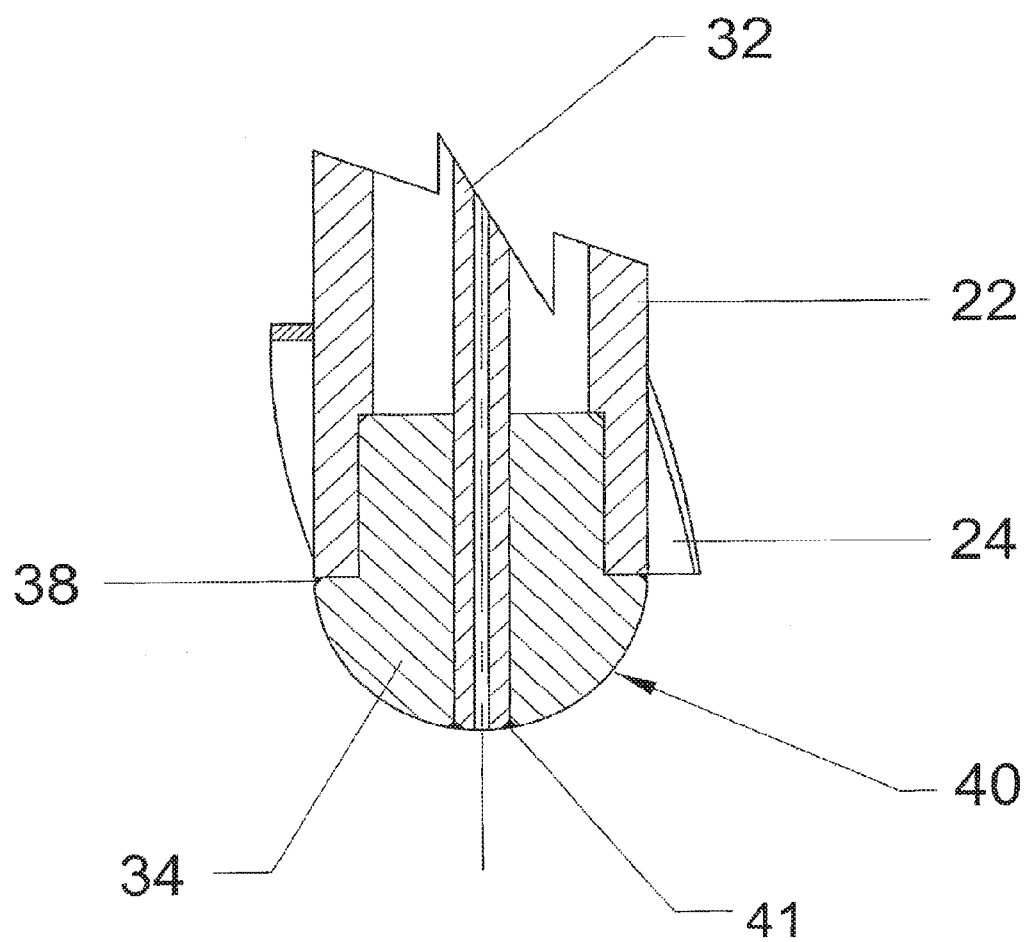
FIG. 3 is a more detailed section of the hemispherical inlet end shown in FIG. 2.

FIG. 3 is a more detailed section of the hemispherical inlet end shown in FIG. 2. Preferably, end member 34 takes the form of a hemispherical insert and is sealed within the lower portion 22 by a circumferential weld 38. The surface finish 40 of the hemispherical insert 34 is machined to give a surface roughness of less than 0.4µ RA; this reduces local turbulence and help prevent the buildup of particulates and contaminants from the process on surface 40. Preferably, the surface finish 40 is further smoothed by the application of the Silcosteel®-AC surface coating or the like. The inlet end of sampling tube 32 is sealed into the hemispherical insert 34 by means of a circumferential weld 41. The internal surface of the sampling tube 32 is preferably treated, with an electro-polishing treatment, to reduce surface roughness; and for critical analysis conditions may be further treated with either the Silcosteel® or Sulfinert® surface coating or the like. Sampling tube 32 may comprise PTFE or a similar inert material; such as PVDF, in which case weld 41 would be replaced by an appropriate adhesive bond.

Figure 4:
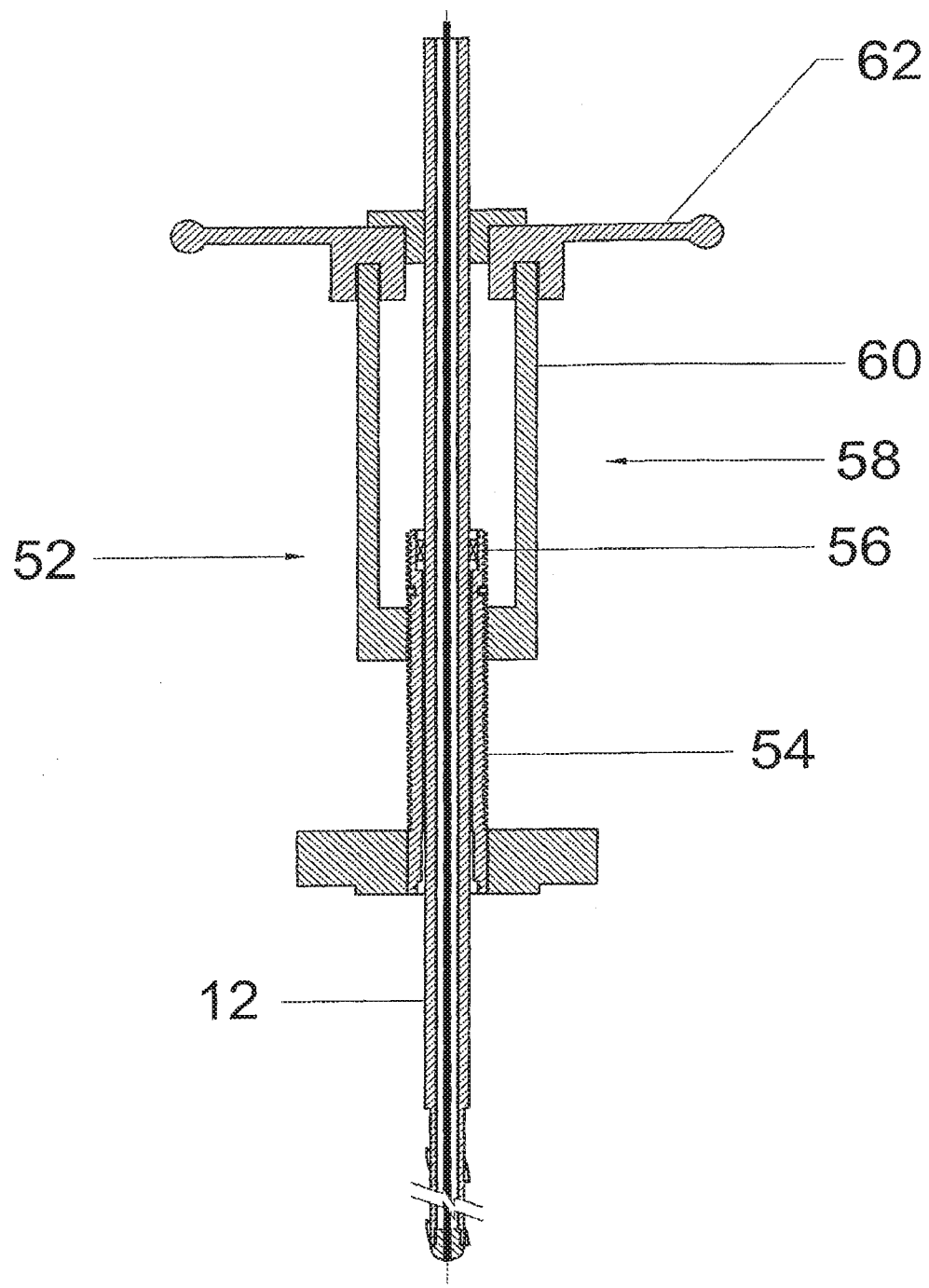
FIG. 4 shows a section of an example of a retractable gas sampling probe, according to a second embodiment of the invention.

FIG. 4 shows a section of an example of a retractable gas sampling probe, according to a second embodiment of the invention. In this embodiment main body 12 is not directly fixed to a flange 50 but rather is fixed to a flange by an adjustment/retraction means 52. This adjustment means can be any of several known to the skilled artisan; for example it may comprise a threaded tube 54 fixed at one end to flange 50 through which the main body 12 passes; tube 54 having fluid sealing means 56; for example an O-ring seal. Adjustment means 52 further comprises an arm member that comprises cylindrical portion 6o and arm portions 62. Cylindrical portion 60 has a threaded bore that in use co-operates with the outer thread of tube 54 to allow the position of the probe 10 to be adjusted in an axial direction.

The use of the helical fins 24 and small bore lining tube 32 to such retractable probes is generally more beneficial than to fixed probes because they generally have longer unsupported probe lengths making it more susceptible to the effects of vortex shedding and the probe itself is much longer making the internal volume that much greater.

Figure 5:
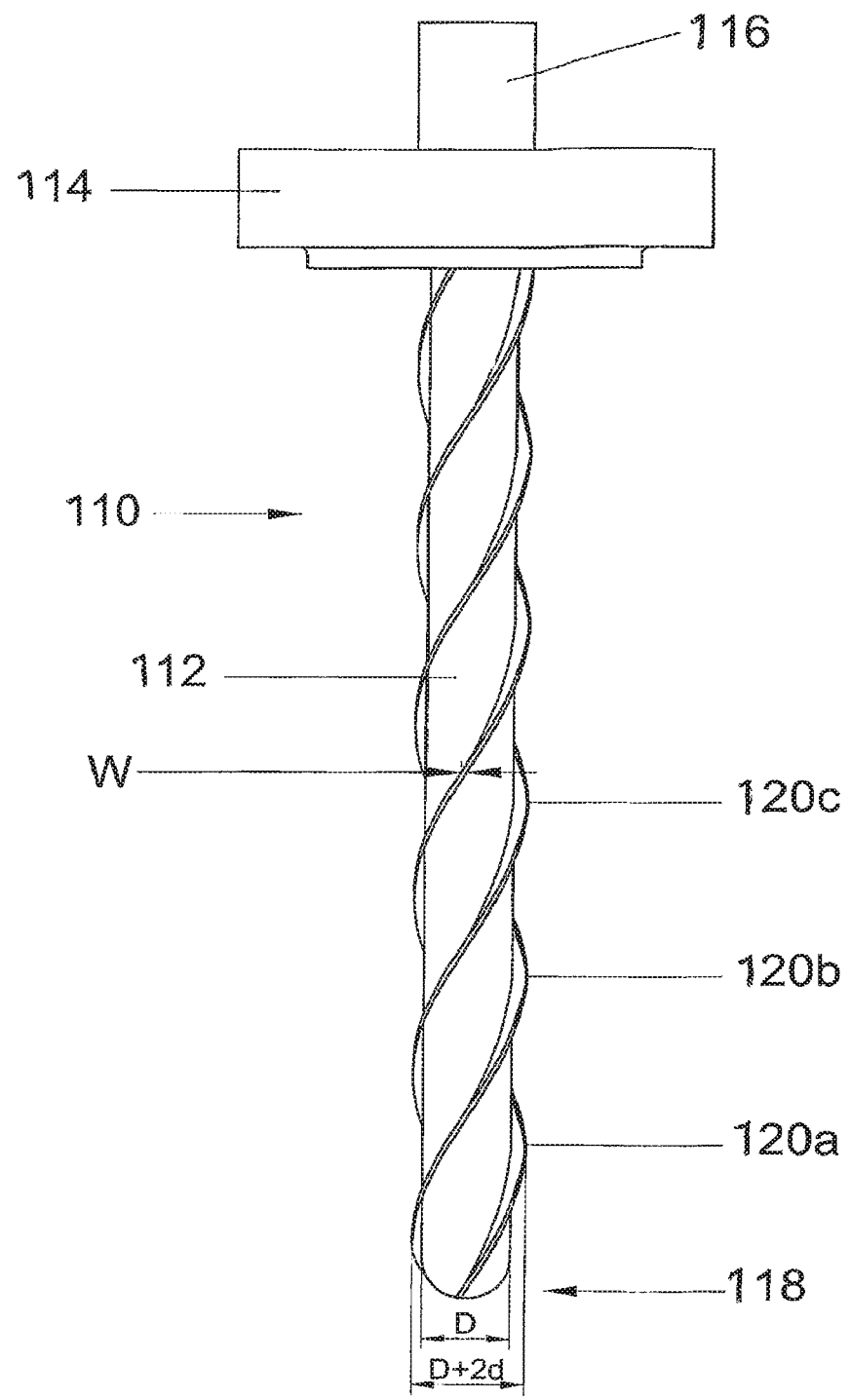
FIG. 5 shows a side view of a thermowell according to a third embodiment of the invention.

FIG. 5 shows a thermowell according to a third embodiment of the invention. The thermowell 110 comprises an elongated tube 112 with an internal bore (not shown) and sealed with a hemispherically shaped cap 118 at one end. The other end of tube 112 is connected via a flange 114 to temperature probe inlet 116. Inlet 116 comprises a short tube through which a temperature probe such as a thermocouple or thermistor may be inserted into the internal bore of tube 112 such that, the sensing element of the probe is near the bottom of the internal bore and so in close thermal proximity to end cap 118.

Tube 112 further comprises three helically arranged fins 120a, 120b, 120c each fin being of width W and depth d. In this case the fins trace a three dimensional curve round and simultaneously advancing along a cylinder. However, tube 112 may have a shape other than a cylinder; for example it may have a somewhat conical portion. The fins are shown extending along the entire length of elongated tube 112; however; the fins may alternatively extend only part way along the length of tube 112. The fins 120 may be integrally formed with or attached to tube 112.

It has been found that in use such fins may reduce or eliminate vortex shedding from the thermowell; this is a significant benefit as such vortex shedding can result in cyclic forces that will damage the thermowell, or even the temperature sensor itself: especially if the period of such cycles is at or near the resonant frequency of the thermowell. While the fin preferably has a cross section with a sharp edge; for example a rectangular cross section other shaped cross sections are possible; for example the cross section may have a semicircular outer portion. Preferably the width (W) of the fin is in the range 0.005 D to 0.2 D, where D is the external diameter or width of the tube. Preferably, the depth of the fin (d) is in the range 0.05 D to 0.5 D. The pitch of each helical fin is preferably in the range D to 20 D, more preferably 2 D to 10 D and most, preferably 3 D to 7 D. It has been found that fins having dimensions within these ranges are particularly effective in reducing or eliminating such vortex shedding.

Figure 6:
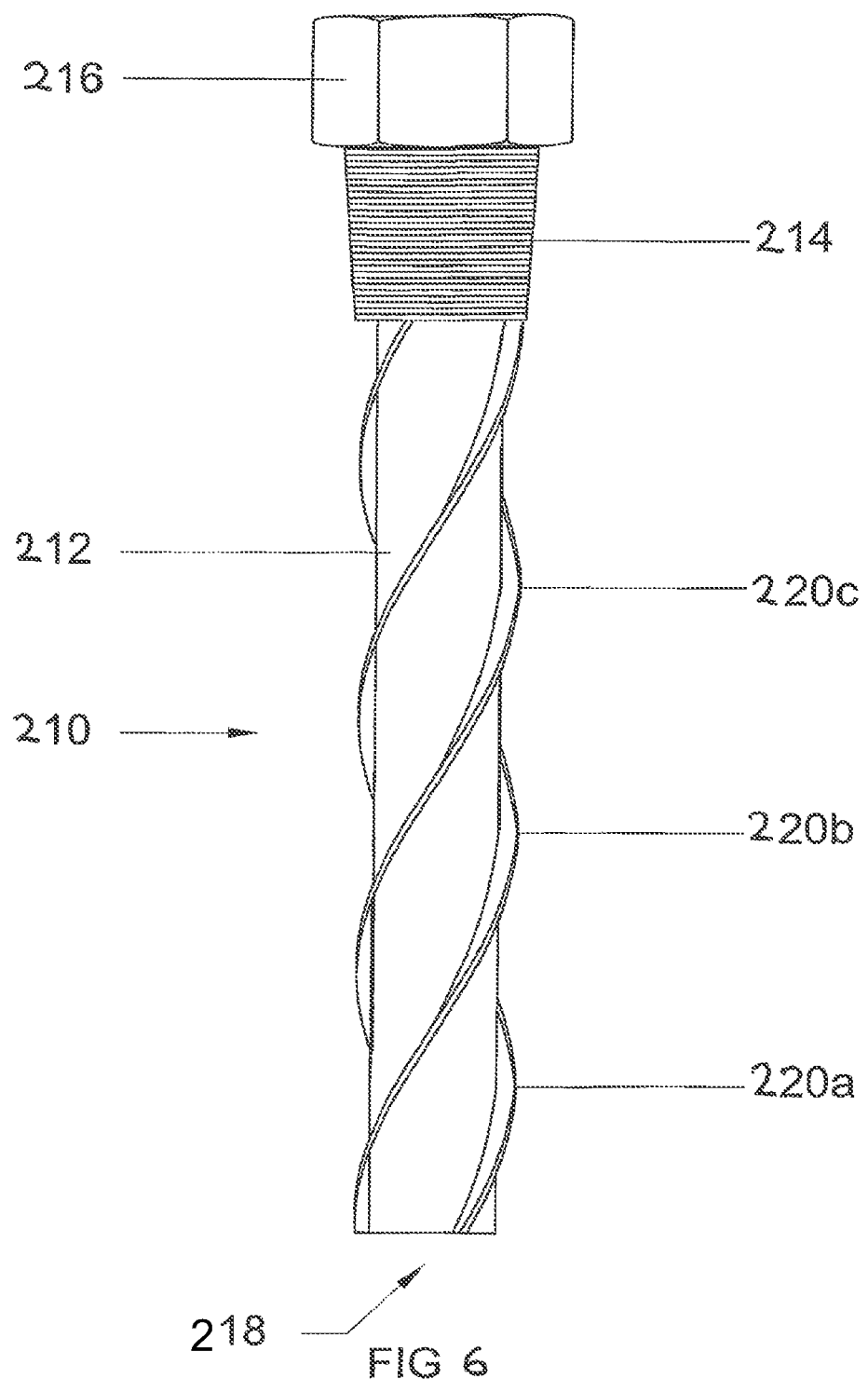
FIG. 6 shows a side view of a thermowell according to a fourth embodiment of the invention.

FIG. 6 shows a fourth embodiment of the invention. In this embodiment the thermowell 210 comprises a cylindrical tube 212 with a flat closed end 218 at one end of the tube and a threaded 214 hexagonal connector 216 at the other. Again, connector 216, threaded portion 214 and tube 212 have an internal bore (not shown) that in use accommodates a temperature sensor. In this embodiment three helical fins 220a, 220b and 220c are attached or formed to the outer surface of tube 212.

Figure 7:
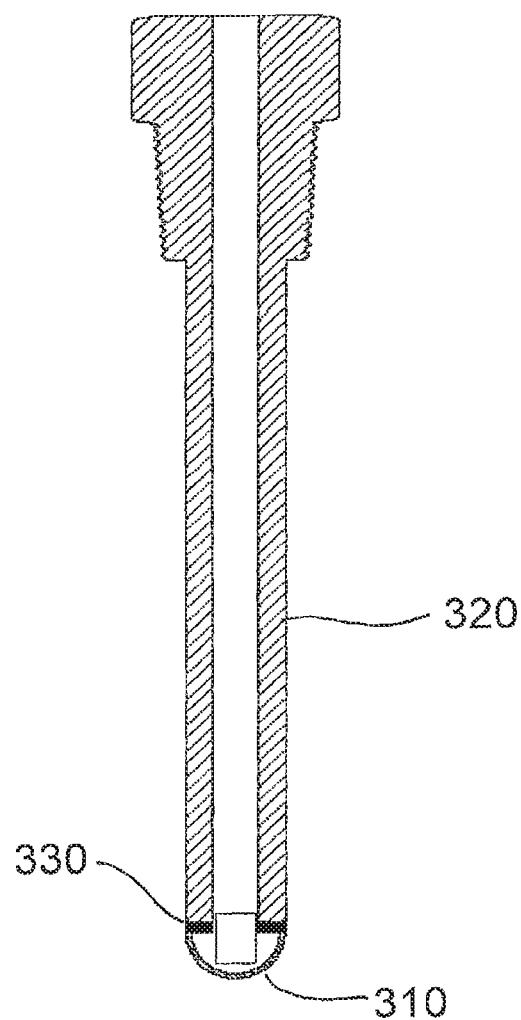
FIG. 7 shows a side view in cross section of a thermowell according to a fifth embodiment of the invention.

FIG. 7 shows a thermowell where the tip 310 of the thermowell, which is the active portion in providing the measurement/thermometry requirements, is made of a higher conductivity material than the main body 320. Further tip 310 may be made of a thinner section material than the main body 320. Ideally tip 310 is thermally separated or partially thermally separated from main, body 320 by a thermal barrier 330. Tip 310 is attached to main body 320 by means such as screwing, gluing, soldering, welding or any appropriate method suitable for the application.

Figure 8:
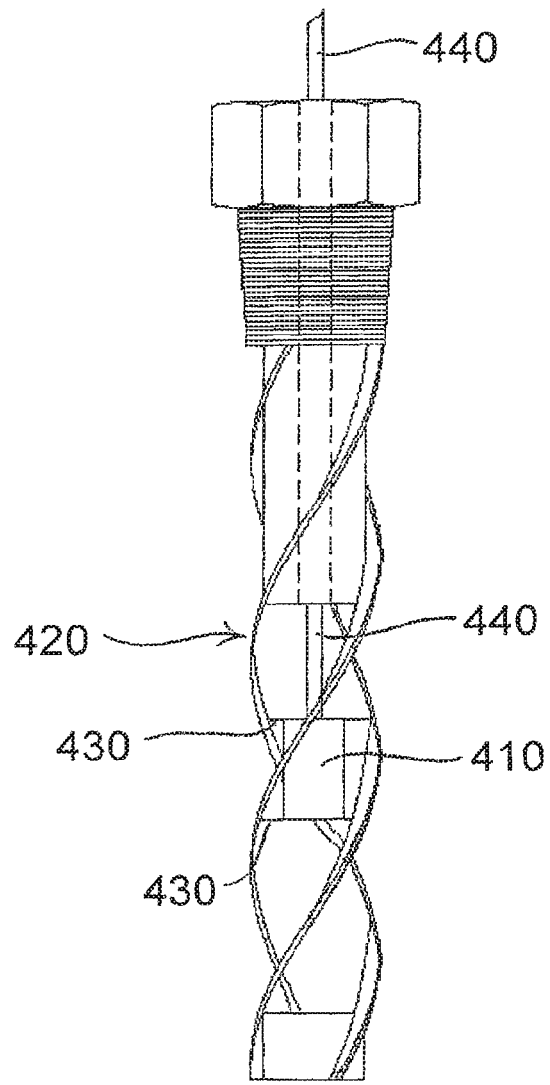
FIG. 8 shows a side view of a thermowell according to a sixth embodiment of the invention.

FIG. 8 shows a thermowell were the measurement/thermometry requirements are; provided by a capsule 410, containing the primary temperature measuring device (not shown) which is held, supported and attached, to the containment means, by main body 420. In this case the main body 420 is of an open lattice structure allowing the medium whose temperature is to be measured to be in thermal contact with the capsule 410. Preferably, thermal capsule 410 is thermally separated or partially thermally separated from main body 420 by a thermal barrier 430. In this embodiment the means of transmitting the measured temperature from the primary measuring device contained in capsule 410 may be a conduit or cable 440 which is sealed/connected to main body 420 at a distance from capsule 410 thereby reducing conductivity loss.

The foregoing merely illustrates the principles of this invention, and various modifications can be made by persons of ordinary skill in the art without departing from the scope and spirit of this invention.

What is claimed is:

1. An insertion-type probe main body for insertion into a pipe transporting gas, the probe main body comprising:
    an elongate upper tubular portion;
    an elongate lower tubular portion which is integral with and having a diameter smaller than the upper tubular portion;
    a bore which extends between the upper and lower tubular portions; and
    a plurality of helical fins integrally formed on the lower tubular portion of the insertion-type probe main body and which wind along and around an outer surface of the lower tubular portion and which overlap each other,
    wherein a radial extension of the lower tubular portion plus helical fins corresponds to an external radius of the upper tubular portion, so that the helical fins extend in a streamline fashion from the upper tubular portion; and
    wherein a lateral outer edge of the helical fins is substantially flush with an outer surface of the elongate upper tubular portion.

2. The insertion-type probe main body of claim 1, wherein the upper elongate tubular portion includes a flange.

3. The insertion-type probe main body of claim 1, wherein the upper elongate tubular portion includes a threaded connector.

4. The insertion-type probe main body of claim 1, wherein each of the plurality of helical fins originates on the outer surface of the lower tubular portion at a separate location.

5. The insertion-type probe main body of claim 1, wherein the outer surface of an inlet end of the elongate lower tubular portion is treated using a passivation process to reduce surface activity and particulate adhesion.

6. The insertion-type probe main body of claim 1, wherein the bore comprises a cross sectional area between 0.1 mm$^2$ to 30 mm$^2$.

7. A method of forming an insertion-type probe main body for insertion into a pipe transporting gas, the method comprising the steps of:
    integrally forming a plurality of helical fins on an elongate lower tubular portion of the insertion-type probe main body which wind along and around an outer surface of the lower tubular portion and which overlap each other,
    wherein an elongate upper tubular portion integrally extending from the lower tubular portion has a diameter greater than the elongate lower tubular portion, and
    wherein the helical fins meet the elongate upper tubular portion such that a lateral outer edge of the helical fins is substantially flush with an outer surface of the elongate upper tubular portion.

8. An insertion-type probe main body which is insertable into a pipe or vessel containing fluid, the probe main body comprising:
    an elongate first tubular portion and an elongate second tubular portion, the elongate first tubular portion being integral with the second tubular portion;
    a bore which extends between the first and second tubular portions of the insertion-type probe main body; and
    a plurality of helical fins integrally formed on the first tubular portion and which wind along and around an outer surface of the first tubular portion and which overlap each other,
    wherein each of the plurality of helical fins originates on the outer surface of the first tubular portion at a separate location; and
    wherein a lateral outer edge of the helical fins is substantially flush with an outer surface of the elongate second tubular portion.

9. The insertion-type probe main body of claim 8, wherein a diameter of the first tubular portion is smaller than the second tubular portion, and wherein a radial extension of the first tubular portion plus helical fins substantially corresponds to an external radius of the second tubular portion, so that the helical fins extend in a streamline fashion from the second tubular portion.

10. The insertion-type probe main body of claim 8, wherein the outer surface of an inlet end of the elongate first tubular portion is treated using a passivation process to reduce surface activity and particulate adhesion.

11. The insertion-type probe main body of claim 8, wherein the bore comprises a cross sectional area between 0.1 mm$^2$ to 30 mm$^2$.

12. The insertion-type probe main body of claim 8, wherein the depth of each of the plurality of helical fins is in the range 0.05D to 0.25D, where D is a diameter of the first tubular portion.

13. A method of forming an insertion-type probe main body for insertion into a pipe or vessel containing fluid, the method comprising the step of:
    integrally forming a plurality of helical fins on an elongate first tubular portion of the insertion-type probe main body which wind along and around an outer surface of the first tubular portion and which overlap each other,
    wherein an elongate second tubular portion integrally extends from the first tubular portion, and
    wherein each of the plurality of helical fins originates on the outer surface of the first tubular portion at a separate location; and
    wherein a lateral outer edge of the helical fins is substantially flush with an outer surface of the elongate second tubular portion.

* * * * *